United States Patent
Yamashita et al.

(12) 
(10) Patent No.: US 6,497,878 B1
(45) Date of Patent: Dec. 24, 2002

(54) TREATMENT OF CEREBRAL DISORDERS BY INHIBITION OF IL-8 BINDING TO RECEPTOR

(75) Inventors: Junkoh Yamashita, Kanazawa (JP); Kiyonobu Ikeda, Kanazawa (JP); Tetsuya Matsumoto, Kanazawa (JP); Kouji Matsushima, Matsudo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/171,629

(22) PCT Filed: Apr. 23, 1997

(86) PCT No.: PCT/JP97/01406

§ 371 (c)(1),
(2), (4) Date: Oct. 19, 1998

(87) PCT Pub. No.: WO97/39775

PCT Pub. Date: Oct. 30, 1997

(30) Foreign Application Priority Data

Apr. 23, 1996 (JP) ................................. 8-137359
Oct. 22, 1996 (JP) ............................... 8-315379

(51) Int. Cl.[7] .......................................... A61K 39/395
(52) U.S. Cl. ................. 424/141.1; 424/145.1; 424/158.1; 514/885
(58) Field of Search ................... 424/145.1, 158.1; 514/885; 530/387.1, 388.23, 389.2, 141.1

(56) References Cited

U.S. PATENT DOCUMENTS 5,440,021 A  *  8/1995 Chuntharapai et al.
6,024,956 A  *  2/2000 Matsushima et al.

FOREIGN PATENT DOCUMENTS

WO   WO 92/04372   *  3/1992
WO   WO 94/18989   *  9/1994
WO   WO 95/23865      9/1995

OTHER PUBLICATIONS

Dorland's Illustrated Medical Dictionary. 27th Edition. W.B. Saunders Co., Philadelphia, 530, 834–835, 857, 1718, 1998.*
The Merck Manual of Diagnosis and Therapy. Berkow, ed., Merck Res. Labs, NJ, pp. 1450–1459, 1992.*
The Merck Manual. 16th edition, Merck Res. Lab., Rahway, NJ, Berkow et al, eds., pp. 1450–1456, 1992.*
Dorland's Illustrated Medical Dictionary, 27th Edition, W.B. Saunders Company, Philadelphia, p. 857, 1988.*
Dorland's Illustrated Medical Dictionary. 27th Edition. W.B. Saunders Co., Philadelphia, 1988.*
Onodera et al., Nippon Rinsho (1994) 52(11):2995–2999.
Sekido et al., Nature (1993) 365:654–657.
Adhesion of flowing neutrophils to cultured endothelial cells after hypoxia and reoxygenation in vitro, g. e. Rainger et al., Am. J. Physiol., (1995) 269 (4, Pt. 2) H1398–H1406.

* cited by examiner

Primary Examiner—Christina Chan
Assistant Examiner—Marianne DiBrino
(74) Attorney, Agent, or Firm—Morrison & Foerster LLP

(57) ABSTRACT

Methods and compositions for treating or preventing cerebral stroke, cerebral infarction, cerebral edema, reperfusion injury and increased cerebral vascular permeability which employ an agent that prevents the binding of IL-8 to its receptor are disclosed.

8 Claims, 3 Drawing Sheets

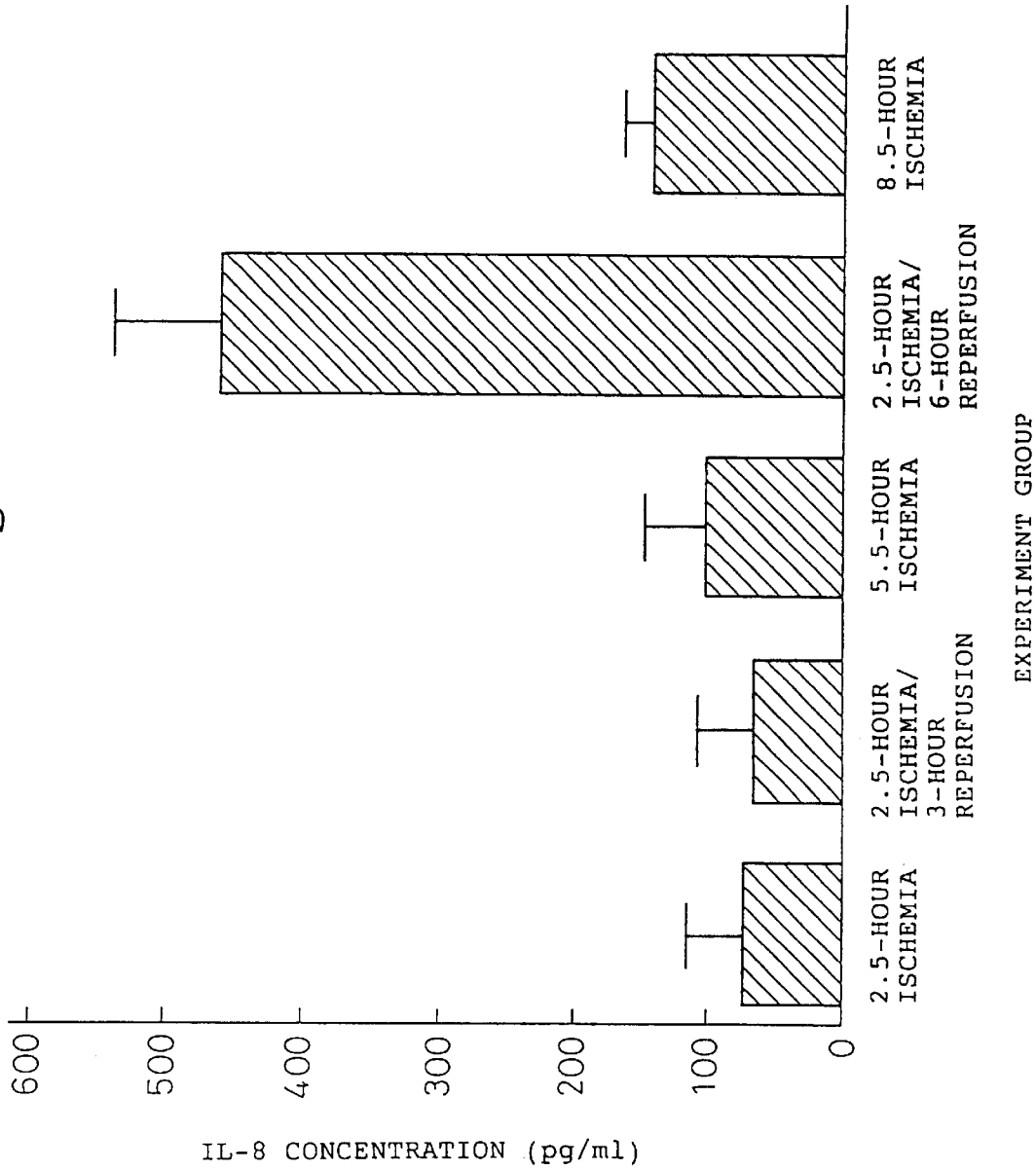

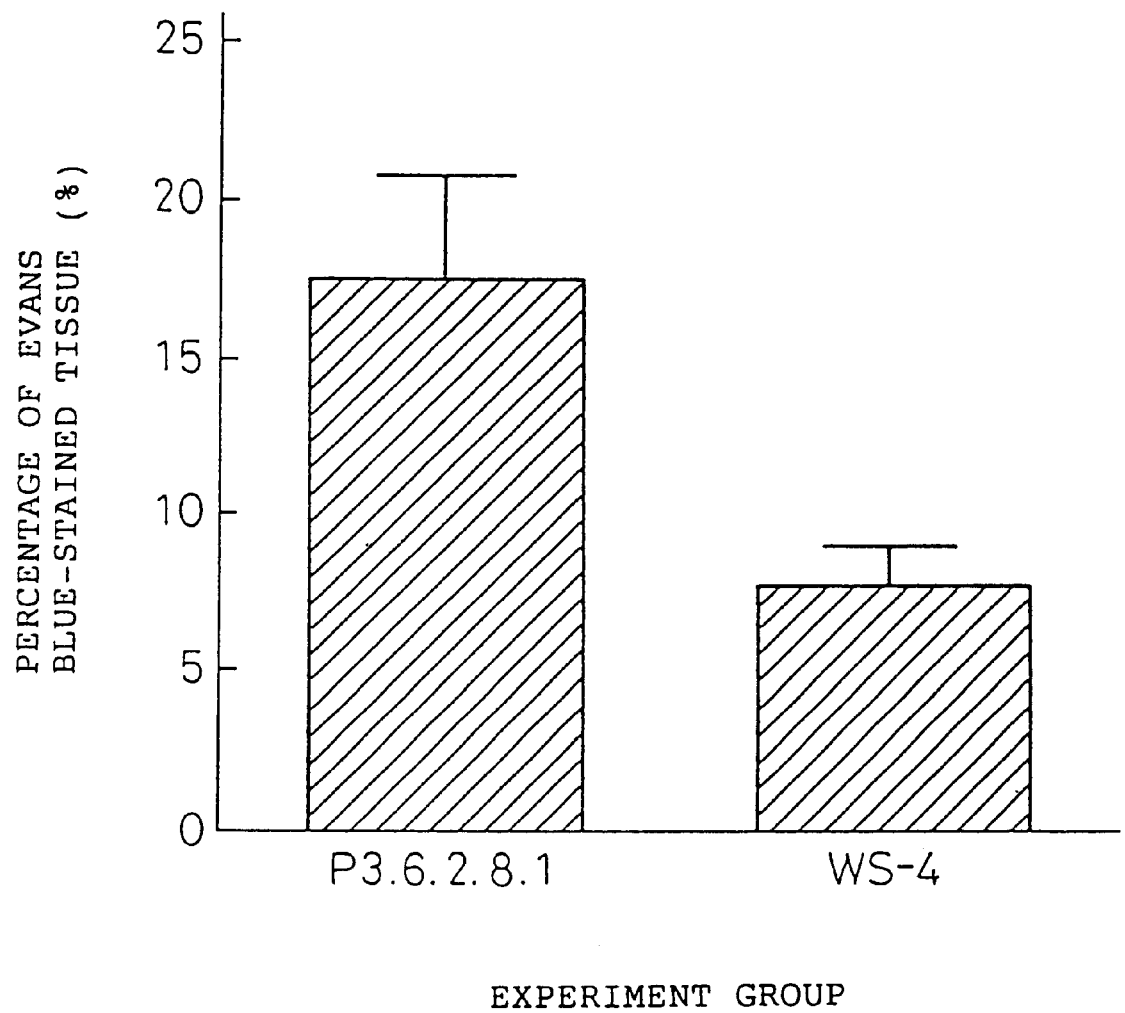

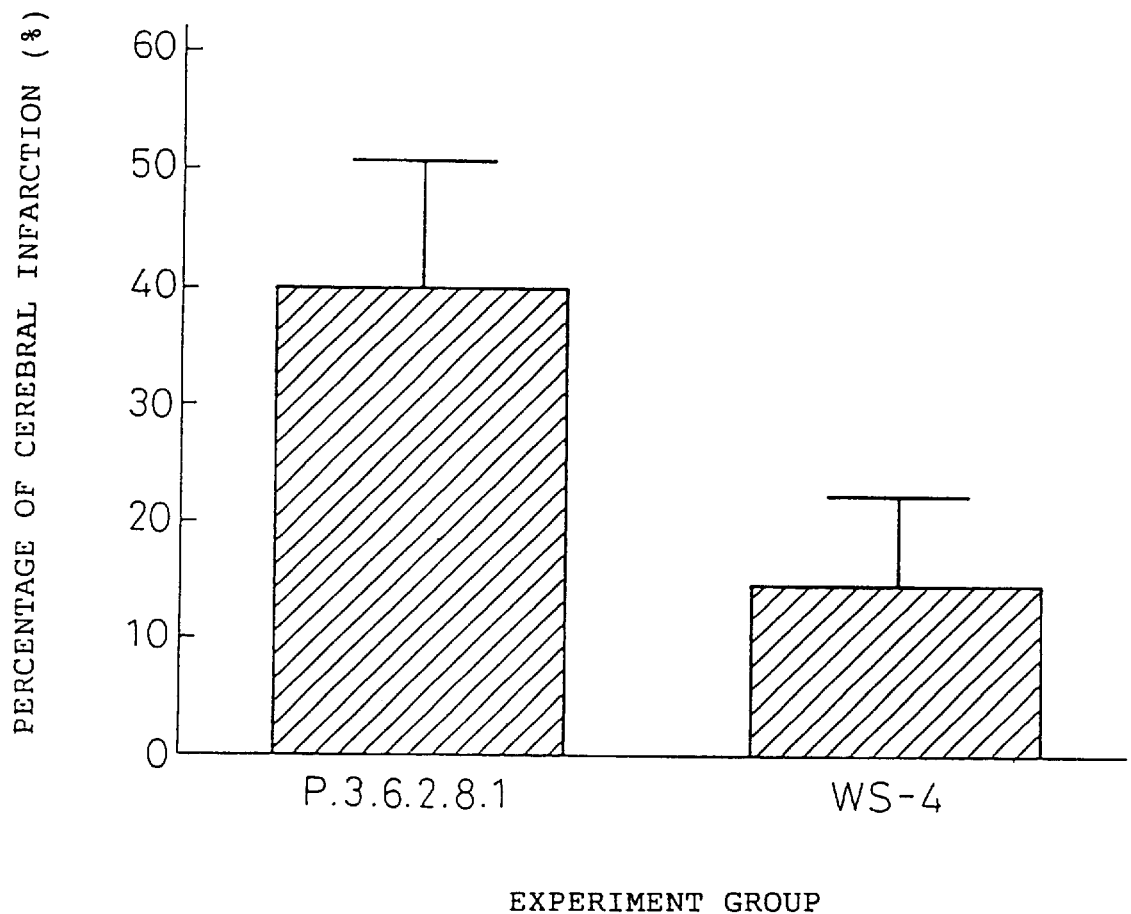

TREATMENT OF CEREBRAL DISORDERS BY INHIBITION OF IL-8 BINDING TO RECEPTOR

TECHNICAL FIELD

The present invention relates to a preventive or therapeutic agent for cerebral stroke comprising an interleukin-8 (IL-8)-binding-inhibition agent as an active ingredient. The present invention also relates to a preventive or therapeutic agent for cerebral edema comprising an IL-8-binding-inhibition agent as an active ingredient. The present invention also relates to a preventive or therapeutic agent for reperfusion injury of cerebral ischemia comprising an IL-8-binding-inhibition agent as an active ingredient. Furthermore, the present. invention relates to a preventive or therapeutic agent for increased cerebral vascular permeability comprising an IL-8-binding-inhibition agent as an active ingredient.

BACKGROUND ART

IL-8 is a protein that belongs to the C-X-C chemokine subfamily and was formerly designated as the monocyte-derived neutrophil chemotactic factor, the neutrophil attractant/activation protein-1, the neutrophil activating factor and the like. IL-8 is a factor that activates neutrophils and provide them with a migratory ability, and is produced by inflammatory cytokines such as IL-1β and TNF-α (Koch, A. E. et al., J. Investig. Med. (1995) 43, 28–38; Larsen, C. G. et al., Immunology (1989) 68, 31–36), mitogens such as PMA and LPS (Yoshimura, T. et al, Proc. Natl. Acad. Sci. U.S.A. (1987) 84, 9233–9237), and heavy metals such as Cadmium (Horiguchi, H. et al., Lymphokine Cytokine Res. (1993) 12, 421–428) in a variety of cells. It is also known that human umbilical endothelial cells under a low oxygen condition express IL-8 (Karakurum, M. et al., J. Clin. Invest. (1994) 93, 1564–1570).

In order for IL-8 to exhibit its biological activity, it is necessary that IL-8 binds to IL-8 receptor and thereby stimulates the cells that are expressing IL-8 receptors. IL-8 receptors that transmit signals into the cell by binding to IL-8 have already been cloned and the amino acid sequences thereof have been elucidated. Human IL-8 receptors include those referred to as IL-8 receptor A (α or 2) and those referred to as IL-8 receptor B (β or 1) (Murphy, P. M. and Tiffany, H. L., Science (1991) 253, 1280–1283; Holmes, W. E. et al., Science (1991) 253, 1278–1280). Both receptors are thought to have a structure that penetrates the cell membrane seven times, and both are associated with GTP-binding proteins in the cytoplasmic domain (Horuk, R., Trends Pharmacol. Sci. (1994) 15, 159–165), and transmit IL-8 signals into the cell. Therefore, inhibition of binding, between IL-8 and IL-8 receptor enables the inhibition of biological activity of IL-8.

The IL-8 binding-inhibition agents so far known include the following substances. As anti-IL-8 antibodies, there are known WS-4 antibody (Ko, Y. et al., J. Immunol. Methods (1992) 149, 227–235), 14E4, 46E5 (Sticherling, M. et al., J. Immunol. (1989) 143, 1628–1634), and human antibody (International Patent Application WO 96/33735), and besides, a polysaccharide (International Patent Application WO 94/18989), a chemical synthetic compound (Sola, F. et al., Invasion Metastasis (1995) 15, 222–231), a peptide fragment (Hayashi, S. et al., J. Immunol. (1995) 154, 814–824), and the like.

With respect to the involvement of IL-8 in reperfusion injury of ischemia, the following findings have been obtained. It has already been reported that in the experimental animal model of reperfusion injury of pulmonary ischemia, the administration of anti-IL-8 antibody at reperfusion following 2 hours of pulmonary ischemia inhibited damages to lung tissues (Sekido, N. et al., Nature (1993) 365, 654–657). On the other hand, though the expression of IL-8 in myocardial tissues after reperfusion has been reported (Ivey, C. L. et al., J. Clin. Invest. (1995) 95, 2720–2728; Kukielka, G. L. et al. J. Clin. Invest. (1995) 95, 89–103), the effect of neutralizing IL-8 is unknown. Rather, it is reported that by administering before reperfusion IL-8 per se that is elevated by reperfusion, the formation of the focus of myocardial infarction is inhibited (Lefer, A. M. et al., Br. J. Pharmacol. (1991) 103, 1153–1159). However, it is unknown whether IL-8 is involved in cerebral infarction, cerebral edema, reperfusion injury of cerebral ischemia, and increased cerebral vascular permeability.

From its mechanism of onset, cerebral apoplexy is classified into the occlusive cerebral vascular injury and the hemorrhagic cerebral vascular injury. The occlusive cerebral vascular injury includes cerebral infarction, and the hemorrhagic cerebral vascular injury includes subarachnoid hemorrhage and cerebral hemorrhage. Cerebral infarction is a condition in which occlusion or decreased perfusion pressure in cerebral and carotid arteries occurred for any reason, thereby causing ischemic necrosis in the brain tissue, and the disease is further divided broadly into the thrombotic, embolic and the hemodynamic infarctions.

The condition in which a sclerotic lesion in the brain arteries combined with increased blood viscosity or decreased perfusion pressure caused anterior occlusion leading to ischemic necrosis is referred to as cerebral thrombosis, the condition in which embolism was formed in the brain artery by intracardiac thrombus or the occasionally ablated mural thrombus of artery is referred to as cerebral embolism, and when the stenosis or occlusion of the cranial and intracranial arteries causes decreased blood flow into the peripheral brain tissues leading to infarction, it is referred to as hemodynamic infarction (Toshio Matobe and Teruo Omae, ed., "Noukekkan Shougai (Cerebral Vascular Injuries)," Life Science Shuppan, 54–55, 1992; Hiroo Imura ed., "Noukekkan Shougai (Cerebral Vascular Injuries)," in Saishin Naikagaku Taikei (Institution of the Latest Internal Medicine), vol. 66, Nakayama Shoten, 28, 1996).

In the brain tissue that has fallen into ischemia because of cerebral infarction, cerebral hemorrhage, or subarachnoid hemorrhage, the formation of ischemic cerebral edema may be observed. In the case of cerebral infarction, cerebral edema appears a few hours after the onset and persists up to one week after the onset. Thereafter cerebral edema gradually decreases and, depending on the scope of the infarct, becomes fixed as the lesion of the infarct during the one to three months after the onset of the disease. In cerebral hemorrhage, cerebral edema becomes manifest in the periphery of hematoma generally about 6 hours after the onset of the disease due to impaired blood flow at the peripheral territory of the disrupted arteries and impaired circulation and tissue necrosis arising from compression by hematoma (Hiroo Imura ed., "Noukekkan Shougai (Cerebral Vascular Injuries)," in Saishin Naikagaku Taikei (Institution of the Latest Internal Medicine), vol. 66, Nakayama Shoten, 289, 1996).

In the case of subarachnoid hemorrhage, delayed spasm is observed 3 days to 3 weeks after hemorrhage, and the spasm is associated with decreased cerebral perfusion pressure which causes delayed cerebral ischemia. Those unresponsive to treatment develop into cerebral infarction, which in severe cases cause ischemic cerebral edema (Hiroo Imura ed., "Noukekkan Shougai (Cerebral Vascular Injuries)," in Saishin Naikagaku Taikei (Institution of the Latest Internal Medicine), vol. 66, Nakayama Shoten, 163, 1996). Cerebral edema causes an increase in the volume of the brain. Since the brain is covered with the hard cranium, cerebral edema, when it surpasses a certain degree, may cause a sudden rise in tissue pressure and intracranial pressure, which eventually aggravates brain disorders and determines the future scope of the lesion of the infarct (Kenji Inamura and Akiro Kaku, Nippon Rinsho Vol. 51, "CT, MRI Jidaino Nosocchu Gaku, Jokan (Stroke in the Age of CT and MRI, the first volume)," Nippon Rinsho (Japan Clinic), 231–239, 1993). When a part of the brain falls into infarction, the functions carried by the region such as recognition, consciousness, sensation, and memory are lost.

Cerebral edema often occurs in head injuries especially brain contusion, acute subdural hematoma, and acute intracranial hematoma. Cerebral edema serves as an enlarged intracranial lesion with a result that local neurological symptoms become manifest, and intracranial swelling and increased pressure lead to the formation of transtentorial herniation and transforaminal herniation in the brain tissue, which becomes fatal (The Japanese edition of Merck Manual, Vol. 1, Medical Book Service, 1405–1406, 1994).

Furthermore, a surgical operation such as craniotomy may be practiced for the purpose of treating head injury, cerebral hemorrhage, subarachnoid hemorrhage, cerebral tumor, and the like. In order to avoid secondary bleeding in these occasions, the blood vessels whose territory is to be treated may be temporarily occluded with an arterial clip etc. to partially block the cerebral blood flow. In such cases, blood flow is resumed after the completion of the desired surgery, when reperfusion injury of ischemia may occur. Furthermore, among the surgical processes for treatment of cerebral infarction is anastomosis between the superficial temporal artery and the middle cerebral artery. In such cases as well, anastomosis is performed under temporal hemostasis, and blood flow is resumed after the desired surgery, when reperfusion injury of ischemia may occur.

As hereinabove described, the prevention and treatment of cerebral stroke and cerebral edema that affects the prognosis of life and quality of life of the patient is a clinically very important challenge. At present anti platelet agents and agents for improving cerebral circulation metabolism are being administered for treatment of cerebral infarction. Although some anti-platelet agents are effective for treatment of the acute phase of cerebral thrombosis, they are contraindicated for patients with cerebral hemorrhage or cerebral infarction who exhibit similar symptoms, since they accelerate hemorrhagic cerebral infarction, and thereby careful diagnosis of the disease type is required before use (Yukihito Shinohara, "medicina," Igaku Shoin, Vol. 32, No. 11, 2217–2219, 1995).

Agents for improving cerebral circulation metabolism are drugs that are administered during the chronic phase at one month after an attack of cerebral infarction and after, and are considered to be undesirable for use during the acute phase (Masakuni Kameyama ed., "Nosocchu Chiryo Manual (Manual of Cerebral Stroke Treatment)," Igaku Shoin, 172–173, 1991). In recent years, for the purpose of resuming blood flow in areas that have not yet fallen into irreversible cell death during the super acute phase after the onset, thrombolytic therapy, bypass surgery, thromboendarterectorny, embolectomy and the like have been performed. Unlike myocardial infarction, however, the resumption of blood flow after an irreversible damage was imparted to the brain tissue may cause reperfusion injury of ischemia such as increases in hemorrhagic infarction and cerebral edema in which tissue damage is aggravated, providing a new problem to be solved (Yasushi Okada, "Sinkei Kenkyuno Shinpo (Advances in Neurological Studies)," Igaku Shoin, Vol. 40, No. 4, 655–665, 1996; Akira Takahashi, "medicina," Igaku Shoin, Vol. 32, No. 11, 2261–2263, 1995).

As hereinabove stated, the drugs currently used during the acute phase of cerebral infarction may have side effects such as hemorrhagic infarction and reperfusion injury of ischemia, or may have limitations in the indicated pathological conditions and the timing of administration when the therapeutic effects can be expected, and therefore are not satisfactory.

On the other hand, though treatment of cerebral edema relies on the administration of a hypertonic solution, a steroid, or others in combination with hyperpnea and cerebrospinal fluid drainage, its effects are in most cases transient, and its eventual effects of treatment are not very promising (Masakuni Kameyama ed., "Nosocchu Chiryo Manual (Manual of Cerebral Stroke Treatment)," Igaku Shoin, 34–36, 1991).

It is therefore desired to develop a drug having a completely new mechanism different from the conventional etiology as a method of preventing or treating cerebral infarction, cerebral edema, reperfusion injury of cerebral ischemia during reperfusion therapy, or reperfusion injury of cerebral ischemia associated with reperfusion after transient blocking of cerebral blood flow during surgery.

It is an object of the present invention to provide a new preventive or therapeutic agent for such diseases.

Disclosure of the Invention

As a result of an intensive study to provide such a preventive or therapeutic agent, the applicants have found that an IL-8 binding-inhibition agent can attain the desired object and thereby have completed the present invention.

Thus, the present invention provides a preventive or therapeutic agent for cerebral stroke comprising an IL-8 binding-inhibition agent as an active ingredient.

The present invention also provides a preventive or therapeutic agent for cerebral infarction comprising an IL-8 binding-inhibition agent as an active ingredient.

The present invention also provides a preventive or therapeutic agent for cerebral thrombosis comprising an IL-8 binding-inhibition agent as an active ingredient.

The present invention also provides a preventive or therapeutic agent for cerebral embolism comprising an IL-8 binding-inhibition agent as an active ingredient.

The present invention also provides a preventive or therapeutic agent for hemodynamic infarction comprising an IL-8 binding-inhibition agent as an active ingredient.

The present invention also provides a preventive or therapeutic agent for, hemorrhagic cerebrovascular disorders comprising an IL-8 binding-inhibition agent as an active ingredient.

The present invention also provides a preventive or therapeutic agent for cerebral hemorrhage comprising an IL-8 binding-inhibition agent as an active ingredient.

The present invention also provides a preventive or therapeutic agent for subarachnoid hemorrhage comprising an IL-8 binding-inhibition agent as an active ingredient.

The present invention also provides a preventive or therapeutic agent for cerebral edema comprising an IL-8 binding-inhibition agent as an active ingredient.

The present invention also provides a preventive or therapeutic agent for ischemic cerebral edema comprising an IL-8 binding-inhibition agent as an active ingredient.

The present invention also provides a preventive or therapeutic agent for cerebral edema associated with head injuries comprising an IL-8 binding-inhibition agent as an active ingredient.

The present invention also provides a preventive or therapeutic agent for reperfusion injury of cerebral ischemia comprising an IL-8 binding-inhibition agent as an active ingredient.

The present invention also provides a preventive or therapeutic agent for reperfusion injury of cerebral ischemia associated with reperfusion after transient blocking of cerebral blood flow during surgery comprising an IL-8 binding-inhibition agent as an active ingredient.

The present invention also provides a preventive or therapeutic agent for reperfusion injury of cerebral ischemia associated with thrombolytic therapy comprising an IL-8 binding-inhibition agent as an active ingredient.

The present invention also provides a preventive or therapeutic agent for increased vascular permeability comprising an IL-8 binding-inhibition agent as an active ingredient.

The present invention also provides a preventive or therapeutic agent for cerebral stroke comprising anti-IL-8 antibody as an active ingredient.

The present invention also provides a preventive or therapeutic agent for cerebral infarction comprising anti-IL-8 antibody as an active ingredient.

The present invention also provides a preventive or therapeutic agent for cerebral thrombosis comprising anti-IL-8 antibody as an active ingredient.

The present invention also provides a preventive or therapeutic agent for cerebral embolism comprising anti-IL-8 antibody as an active ingredient.

The present invention also provides a preventive or therapeutic agent for hemodynamic infarction comprising anti-IL-8 antibody as an active ingredient.

The present invention also provides a preventive or therapeutic agent for hemorrhagic cerebrovascular disorders comprising anti-IL-8 antibody as an active ingredient.

The present invention also provides a preventive or therapeutic agent for cerebral hemorrhage comprising anti-IL-8 antibody as an active ingredient.

The present invention also provides a preventive or therapeutic agent for subarachnoid hemorrhage comprising anti-IL-8 antibody as an active ingredient.

The present invention also provides a preventive or therapeutic agent for cerebral edema comprising anti-IL-8 antibody as an active ingredient.

The present invention also provides a preventive or therapeutic agent for ischemic cerebral edema comprising anti-IL-8 antibody as an active ingredient.

The present invention also provides a preventive or therapeutic agent for cerebral edema associated with head injuries comprising anti-IL-8 antibody as an active ingredient.

The present invention also provides a preventive or therapeutic agent for reperfusion injury of cerebral ischemia comprising anti-IL-8 antibody as an active ingredient.

The present invention also provides a preventive or therapeutic agent for reperfusion injury of cerebral ischemia associated with reperfusion after transient blocking of cerebral blood flow during surgery comprising anti-IL-8 antibody as an active ingredient.

The present invention also provides a preventive or therapeutic agent for reperfusion injury of cerebral ischemia associated with thrombolytic therapy comprising anti-IL-8 antibody as an active ingredient.

The present invention also provides a preventive or therapeutic agent for increased vascular permeability comprising anti-IL-8 antibody as an active ingredient.

The present invention also provides a preventive or therapeutic agent for cerebral infarction, cerebral edema, reperfusion injury of cerebral ischemia, and increased cerebral vascular permeability comprising a monoclonal antibody against IL-8 as an active ingredient.

The present invention also provides a preventive or therapeutic agent for cerebral infarction, cerebral edema, reperfusion injury of cerebral ischemia,.and increased cerebral vascular permeability comprising an antibody against mammalian IL-8 as an active ingredient.

The present invention also provides a preventive or therapeutic agent for cerebral infarction, cerebral edema, reperfusion injury of cerebral ischemia, and increased cerebral vascular permeability comprising an antibody against human-IL-8 as an active ingredient.

The present invention also provides a preventive or therapeutic agent for cerebral infarction, cerebral edema, reperfusion injury of cerebral ischemia, and increased cerebral vascular permeability comprising WS-4 antibody against IL-8 as an active ingredient.

The present invention also provides a preventive or therapeutic agent for cerebral infarction, cerebral edema, reperfusion injury of cerebral ischemia, and increased cerebral vascular permeability comprising a humanized or chimeric antibody against IL-8 as an active ingredient.

The present invention further provides a preventive or therapeutic agent for cerebral infarction, cerebral edema, reperfusion injury of cerebral ischemia, and increased cerebral vascular permeability comprising humanized WS-4 antibody against IL-8 as an active ingredient.

BRIEF EXPLANATION OF DRAWINGS

FIG. 1 is a graph showing a time course of the amount of IL-8 produced in the brain tissue of the middle cerebral artery permanent occlusion model and the middle cerebral artery ischemia reperfusion model.

FIG. 2 is a graph which compares the inhibitory effect of WS-4 antibody on disruption of the blood brain barrier in the middle cerebral artery 2.5-hour ischemia and 6-hour reperfusion model with that of the negative control P3.6.2.8.1 antibody using increased vascular permeability as an index.

FIG. 3 is a graph which compares the inhibitory effect of WS-4 antibody on the volume of the infarct in the middle cerebral artery 2.5-hour ischemia and 12-hour reperfusion model with that of the negative control P3.6.2.8.1 antibody.

MODE FOR CARRYING OUT THE INVENTION

1. IL-8 Binding-inhibition Agents

An IL-8 binding-inhibition agent for use in the present invention may be of any origin, any kind, and any form, as long as it has a therapeutic or preventive effect on cerebral stroke, cerebral edema, reperfusion injury of cerebral ischemia, or increased cerebral vascular permeability.

An IL-8 binding-inhibition agent for use in the present invention is a substance that inhibits the binding of IL-8 to IL-8 receptor. Specifically it is a substance that blocks signal transmission by IL-8 by binding to IL-8, which in turn inhibits the biological activity of IL-8.

Human IL-8 undergoes different processing at the N-terminal end. However, as a target of an IL-8 binding-inhibition agent for use in the present invention, the number of amino acid residues of IL-8 is not limited as long as it retains the biological activity of IL-8.

On the other hand, human IL-8 receptors occur as those referred to as IL-8 receptor A (α or 2) and those referred to as IL-8 receptor B (β or 1). However, as the receptor the binding of IL-8 to which is inhibited by an IL-8 binding-inhibition agent for use in the present invention, its type does is not limited as long as it induces the biological activity of IL-8.

As an IL-8 binding-inhibition agent for use in the present invention, anti-IL-8 antibody is most preferred and it only requires the confirmation of its preventive or therapeutic effects according to the following methods.

2. Anti-IL-8 Antibody

Anti-IL-8 antibodies for use in the present invention may be of any origin, any kind (monoclonal or polyclonal), and any form, as long as it has a preventive or therapeutic effect against cerebral stroke, cerebral edema, reperfusion injury of cerebral ischemia, or increased cerebral vascular permeability.

Anti-IL-8 antibodies for use in the present invention can be obtained as polyclonal or monoclonal antibodies using known methods. As the anti-IL-8 antibodies for use in the present invention, monoclonal antibodies of, in particular, mammalian origin, are preferred. Monoclonal antibodies of mammalian origin include those produced by hybridomas or hosts which have been transformed with expression vectors containing genetically engineered antibody genes. The antibody, via binding to IL-8, blocks the binding to IL-8 receptor expressed on neutrophils etc. and thereby inhibits signal transmission of IL-8, and is therefore an antibody which inhibits the biological activity of IL-8.

Examples of such antibodies include WS-4 antibody (Ko, Y. et al., J. Immunol. Methods (1992) 149, 227–235) and DM/C7 antibody (Mulligan, M. S. et al., J. Immunol. (1993) 150, 5585–5595), Pep-1 antibody and Pep-3 antibody (International Patent Application WO 92/04372), or 6G4.2.5 antibody and A5.12.14 antibody (International Patent Application WO 95/23865; Boylan, A. M. et al., J. Clin. Invest. (1992) 89, 1257–1267). Among them, WS-4 antibody is most preferred.

Incidentally, the hybridoma cell line which produces WS-4 antibody has been internationally deposited under the provisions of the Budapest Treaty as mouse hybridoma WS-4 on Apr. 17, 1996 with the National Institute of Bioscience and Human-Technology, Agency of Industrial Science and Technology, of 1–3, Higashi 1-chome, Tsukuba city, Ibaraki pref., Japan, as FERM BP-5507.

IL-8 used as the sensitizing antigen for obtaining antibody can be obtained using the respective IL-8 gene/amino acid sequence as disclosed in Matsushima, K. et al., J. Exp. Med. (1988) 167, 1883–1893 for human IL-8, in Yoshimura, T. and Johnson, D. G., J. Immunol. (1993) 151, 6225–6236 for guinea pig IL-8, in Goodman, R. B. et al., Biochemistry (1992) 31, 10483–10490 for porcine IL-8, in Harada, A. et al., Int. Immunol. (1993) 5, 681–690 for rabbit IL-8, in Ishikawa, J. et al., Gene (1993) 131, 305–306 for canine IL-8, Seow, H. F. et al., Immunol. Cell Biol. (1994) 72, 398–405 for sheep IL-8, and Villinger, F. et al, J. Immunol. (1995) 155, 3946–3954 for monkey IL-8.

It is known that human IL-8 is produced in a variety of cells and undergoes different processing at the N-terminal end (Leonard, E. J. et al., Am. J. Respir. Cell. Mol. Biol. (1990) 2, 479–486). Though an IL-8 that has 79, 77, 72, 71, 70 or 69 amino acid residues has been known so far, the number of amino acid residues is not limited in any way so long as the IL-8 can be used as the antigen for obtaining anti-IL-8 antibody which is used in the present invention.

The gene sequence of IL-8 is inserted into a known expression vector to transform an appropriate host cell. From the host cell or the culture supernatant thereof, the desired IL-8 protein is purified using a known method, and the purified IL-8 protein may be used as the sensitization antigen.

3. Antibody-producing Hybridoma

Hybridomas producing monoclonal antibodies can be basically constructed using a known procedure as described bellow. Thus, IL-8 is used as a sensitizing antigen and is immunized in the conventional method of immunization. The immune cells thus obtained are fused with known parent cells in the conventional cell fusion process, and then screened by the conventional screening method to screen monoclonal antibody-producing cells.

Preferably mammals to be immunized with the sensitization antigen are selected in consideration of their compatibility with the parent cells for use in cell fusion generally and they generally include, but are not limited to, rodents such as mice, rats, hamsters, and the like.

Immunization of animals with a sensitization antigen is carried out using known methods. A general method, for example, includes intraperitoneal or subcutaneous administration of a sensitization antigen to the mammal. Specifically, a sensitization antigen which was diluted and suspended in an appropriate amount of phosphate buffered saline (PBS) or physiological saline etc. is mixed with an appropriate amount of a common adjuvant such as Freund's complete adjuvant. After being emulsified, it is preferably administered to a mammal for several times every 4 to 21 days. Additionally a suitable carrier may be used at the time of immunization of the sensitization antigen.

After the immunization and confirmation of the increase in the desired antibody levels in the serum by a conventional method, the immune cells are taken out from the mammal and are subjected to cell fusion, in which preferred immune cells include in particular the spleen cells.

The mammalian myeloma cells as the other parent cells which are subjected to cell fusion with the above-mentioned immune cells preferably include various known cell lines such as P3 (P3x63Ag8.653) (Kearney, J. F. et al., J. Immunol. (1979) 123, 1548–1550), P3x63Ag8U.1 (Yelton, D. E. et al., Current Topics in Microbiology and Immunology (1978) 81, 1–7), NS-1 (Kohler, G. and Milstein, C., Eur. J. Immunol. (1976) 6, 511–519), MPC-11 (Margulies, D. H. et al., Cell (1976) 8, 405–415), SP2/0 (Shulman, M. et al., Nature (1978) 276, 269–270), F0 (de St. Groth, S. F. and Scheidegger, D., J. Immunol. Methods (1980) 35, 1–21), S194 (Trowbridge, I. S., J. Exp. Med. (1978) 148, 313–323), R210 (Galfre, G. et al., Nature (1979) 277, 131–133) and the like.

Cell fusion between the above immune cells and the myeloma cells may be essentially conducted in accordance with a known method such as is described in Milstein et al. (Galfre, G. and Milstein, C., Methods Enzymol. (1981) 73, 3–46) and the like.

More specifically, the above cell fusion is carried out in the conventional nutrient medium in the presence of, for example, a cell fusion accelerator. As the cell fusion accelerator, for example, polyethylene glycol (PEG), Sendai virus (HVJ) and the like may be used, and an assistant agent such as dimethyl sulfoxide etc. may be added as desired to enhance the efficiency of the fusion.

The preferred ratio of the immune cells and the myeloma cells to be used is, for example, 1 to 10 times more immune cells than the myeloma cells. Examples of culture media to be used for the above cell fusion include RPMI 1640 medium and MEM culture medium suitable for the growth of the above myeloma cell lines, and the conventional culture medium used for this type of cell culture, and besides a serum supplement such as fetal calf serum (FCS) may be added.

In cell fusion, predetermined amounts of the above immune cells and the myeloma cells are mixed wellin the above culture medium, to which a PEG solution previously heated to about 37° C., for example the PEG solution with a mean molecular weight of 1000 to 6000, is added at a concentration of 30 to 60% (w/v) and mixed to obtain the desired fusion cells (hybridomas). Then by repeating the sequential addition of a suitable culture medium and centrifugation to remove the supernatant, cell fusion agents etc. which are undesirable for the growth of the hybridoma can be removed.

The hybridoma is selected by culturing in a conventional selection medium, for example, HAT culture medium (a culture medium containing hypoxanthine, aminopterin, and thymidine). Culturing in the HAT culture medium is continued generally for the period of time sufficient to effect killing of the cells other than the desired hybridoma (non-fusion cells), generally several days to several weeks.

The conventional limiting dilution method is conducted in which the hybridomas producing the desired antibody are screened and monoclonally cloned.

In addition to obtaining the above hybridoma by immunizing non-human animals with an antigen, it is also possible to sensitize human lymphocytes in vitro with IL-8, and the resulting sensitized lymphocytes are fused with a myeloma cell, for example U266, having the ability to divide permanently to obtain the desired human antibody having the activity of binding to IL-8 (Japanese Examined Patent Publication (Kokoku) No. 1-59878). Furthermore, a transgenic animal having a repertoire of human antibody genes is immunized with the antigen IL-8 to obtain anti-IL-8 antibody-producing cells, which are immortalized and then used to obtain human antibody to IL-8 (see International Patent Application WO 92/03918, WO 93/12227, WO 94/02602, WO 94/25585, WO 96/33735 and WO 96/34096).

The monoclonal antibody-producing hybridomas thus constructed can be subcultured in the conventional culture medium, or can be stored for a prolonged period of time in liquid nitrogen.

In order to obtain monoclonal antibodies from said hybridoma, there can be mentioned a method in which said hybridoma is cultured in the conventional method and the antibodies are obtained as the supernatant, or a method in which the hybridoma is transplanted to and grown in a mammal compatible with said hybridoma and the antibodies are obtained as the ascites. The former method is suitable for obtaining high-purity antibodies, whereas the latter is suitable for a large scale production of antibodies.

4. Recombinant Antibody

A recombinant antibody which was produced by the recombinant gene technology in which an antibody gene was cloned from the hybridoma and integrated into a suitable vector which was then introduced into a host can be used in the present invention as monoclonal antibody (see, for example, Borrebaeck, C. A. K. and Larrick, J. W., THERAPEUTIC MONOCLONAL ANTIBODIES, published in the United Kingdom by MACMILLAN PUBLISHERS LTD. 1990).

Specifically, mRNA encoding the variable region (V-region) of anti-IL-8 antibody is isolated from the hybridoma producing anti-IL-8 antibody. The isolation of mRNA is conducted by preparing total RNA using, for example, a known method such as the guanidine ultracentrifuge method (Chirgwin, J. M. et al., Biochemistry (1979) 18, 5294–5299), the AGPC method (Chomczynski, P. and Sacchi, N., Anal. Biochem. (1987) 162, 156–159), and then mRNA is purified from the total RNA using a mRNA Purification kit (Pharmacia) and the like. Alternatively, mRNA can be directly prepared using a QuickPrep mRNA Purification Kit (Pharmacia).

cDNA of the V region of antibody may be synthesized from the obtained mRNA using a reverse transcriptase. cDNA may be synthesized using the AMV Reverse Transcriptase First-strand cDNA Synthesis Kit (Seikagaku Kogyo), and the like. Alternatively, for the synthesis and amplification of cDNA, the 5'-RACE method (Frohman, M. A. et al., Proc. Natl. Acad. Sci. U.S.A. (1988) 85, 8998–9002; Belyavsky, A. et al., Nucleic Acids Res. (1989) 17, 2919–2932) using the 5'-Ampli FINDER RACE Kit (Clontech) and polymerase chain reaction (PCR) may be used.

The desired DNA fragment is purified from the PCR product obtained and may be ligated to vector DNA. Moreover, a recombinant vector is constructed therefrom and then is introduced into E. coli etc., which is selected to prepare the desired recombinant vector. The base sequence of the desired recombinant DNA may be confirmed by a known method such as the dideoxy nucleotide chain termination method.

Once the DNA encoding the V regions of the desired anti-IL-8 antibody have been obtained, it may be ligated to DNA encoding the constant regions (C regions) of the desired antibody, which is then integrated into an expression vector. Alternatively, DNA encoding the V region of the antibody may be integrated into an expression vector which already contains DNA encoding the C region of the antibody.

In order to produce anti-IL-8 antibody for use in the present invention, the antibody gene is integrated into an expression vector so as to be expressed under the control of the expression regulatory region, for example an enhancer and/or a promoter. Subsequently, the expression vector is transformed into a host cell and the antibody is then expressed therein.

The antibody gene may be expressed by integrating separately DNA encoding a heavy chain (H chain) or a light chain (L chain) of the antibody into an expression vector and co-transforming host cell, or by integrating DNA encoding an H chain and an L chain into a single expression vector and transforming host cell (International Patent Application WO 94/11523).

5. Altered Antibody

In accordance with the present invention, artificially altered recombinant antibody such as chimeric antibody and humanized antibody can be used for the purpose of lowering heterologous antigenicity against humans. These altered antibody can be produced using known methods.

Chimeric antibody can be obtained by ligating the thus obtained DNA encoding the V region of antibody other than human antibody to DNA encoding the C region of human antibody, which is then integrated into an expression vector and introduced into a host for production of the antibody therein (see European Patent Application EP 125023, and International Patent Application WO 96/02576). Using this known method, chimeric antibody useful for the present invention can be obtained.

E. coli having the plasmid containing the L chain or the H chain of chimeric WS-4 antibody has been internationally deposited under the provisions of the Budapest Treaty as *Escherichia coli* DHS (HEF-chWS4L-gκ) and *Escherichia coli* JM109 (HEF-chWS4H-gγ1) on Jul. 12, 1944 with the National Institute of Bioscience and Human Technology, Agency of Industrial Science and Technology, of 1–3, Higashi 1-chome, Tsukuba-shi, Ibaraki, Japan, as FERM BP-4739 and FERM BP-4740, respectively.

Humanized antibody which is also called reshaped human antibody has been made by transplanting the complementarity determining region (CDR) of antibody of a mammal other than the human, for example mouse antibody, into the CDR of human antibody. The general recombinant DNA technology for preparation of such antibodies is also known (see European Patent Application EP 125023 and International Patent Application WO 96/02576).

Specifically, a DNA sequence which was designed to ligate the CDRs of mouse antibody with the framework region (FRs) of human antibody is synthesized from several divided oligonucleotides having sections overlapping with one another at the ends thereof, and the oligonucleotides are then synthesized into one integrated DNA by PCR method. The DNA thus obtained is ligated to a DNA encoding a C region of human antibody and then is incorporated into an expression vector, which is introduced into a host for antibody production (see European Patent Application EP 239400 and International Patent Application Wo 96/02576).

For the FRs of a human antibody being ligated with CDRs, the CDRs that have a favorable antigen-binding site are selected. When desired, amino acids in FRs of antibody V region may be substituted so that CDRs of humanized antibody may form an appropriate antigen biding site (Sato, K. et al., Cancer Res. (1993) 53, 851–856).

For chimeric antibody and humanized antibody, a C region of human antibody may be used depending on the purpose. For example, Cγ1, Cγ2, Cγ3, and Cγ4 can be used. The C region of human antibody may also be modified in order to improve the stability of antibody and of the production thereof. For example, when the subclass IgG4 of antibody is chosen, the amino acid sequence CPSCP of part of the hinge region of IgG4 can be converted to the amino acid sequence CPPCP of the hinge region of IgG1 to resolve the structural instability of IgG4 (Angal, S. et al., Mol. Immunol. (1993) 30, 105–108).

Chimeric antibody consists of V regions of antibody derived from a mammal other than the human and C regions derived from human antibody, whereas humanized antibody consists of the CDRs of antibody derived from a mammal other than the human and the FRs and the C region of antibody derived from human antibody. Accordingly, since the amino acid sequences derived from a mammal other than the human are reduced to a minimum in the above antibodies, antigenicity thereof in the human body is reduced so that they are useful as an active ingredient of preventive or therapeutic agents of the present invention.

A preferred embodiment of humanized antibody for use in the present invention includes humanized WS-4 antibody (see International Patent Application WO 96/02576). In the humanized WS-4 antibody, CDRs of the WS-4 antibody derived from a mouse have been ligated to FRs of the human antibody REI for the L chain, and to the FRl-3 of the human antibody VDH26 and the FR4 of the human antibody 4B4 for:the H chain, and part of the amino acid residues of the FR has been substituted to obtain antigen-binding activity.

E. coli having plasmid coding for an L chain or an H chain of humanized WS-4 antibody has been deposited under the provisions of the Budapest Treaty as *Escherichia coli* DH5 (HEF-RVLa-qK) and *Escherichia coli* JM109 (HEF-RVHg-gγ1) on Jul. 12, 1994 with the National Institute of Bioscience and Human Technology, Agency of Industrial Science and Technology, of 1–3, Higashi 1-chome, Tsukuba-shi, Ibaraki, Japan, as FERM BP-4738 and FERM BP-4741, respectively.

6. Modified Antibody

Antibodies for use in the present invention may be fragments of antibody or modified versions thereof as long as they bind to IL-8 and thereby inhibit the activity of IL-8. For example, as fragments of antibody, there may be mentioned Fab, F(ab')2, Fv or single-chain Fv (scFv) in which Fv's of H chain and L chain were ligated via a suitable linker. Specifically antibodies are treated with an enzyme, for example, papain or pepsin, to produce antibody fragments, or genes encoding these antibody fragments are constructed, and then introduced into an expression vector, which is expressed in a suitable host cell (see, for example, Co, M. S. et al., J. Immunol. (1994) 152, 2968–2976; Better, M. and Howitzer, A. H., Methods Enzymol. (1989) 178, 476–496; Pluckthun, A. and Skerra, A., Methods Enzymol. (1989) 178, 497–515; Lamoyi, E., Methods Enzymol. (1986) 121, 652–663; Rousseaux, J. et al., Methods Enzymol. (1986) 121, 663–669; Bird, R. E. and Walker, B. W., Trends Biotechnol. (1991) 9, 132–137).

scFv can be obtained by ligating a V region of an H chain and a V region of an L chain of an antibody. In the scFv, a V region of an H chain and a V region of an L chain are preferably ligated via a linker, preferably a peptide linker (Huston, J. S. et al., Proc. Natl. Acad. Sci. U.S.A. (1988) 85, 5879–5883). A V region of an H chain and a V region of an L chain in the scFv may be derived from any of the above-mentioned antibodies. As the peptide linker for ligating the V regions, any single-chain peptide comprising, for example, 12–19 amino acid residues may be used.

DNA encoding scFv can be obtained using a DNA encoding an H chain or an H chain V region of the above antibody and a DNA encoding an L chain or an L chain V region of the above antibody as the template by amplifying the portion of the DNA encoding the desired amino acid sequence among the above sequences by the PCR technique with the primer pair specifying the both ends thereof, and by further amplifying the combination of DNA encoding the peptide linker portion and the primer pair which defines that both ends of said DNA be ligated to the H chain and the L chain, respectively.

Once DNAs encoding scFv are constructed, an expression vector containing them and a host transformed with said expression vector can be obtained by the conventional methods, and scFv can be obtained using the resultant host by the conventional methods.

These antibody fragments can be produced by obtaining the gene thereof in a similar manner to that mentioned above and by allowing it to be expressed in a host. "Antibody" as used in the claim of the present application encompasses these antibody fragments.

As modified antibodies, anti-IL-8 antibody conjugated with various molecules such as polyethylene glycol (PEG) can be used. "Antibody" as used in the claim of the present application encompasses these modified antibodies. These modified antibodies can be obtained by chemically modifying the obtained antibodies. These methods have already been established in the art.

7. Expression and Production of Anti-IL-8 Antibody

Antibody genes constructed as mentioned above may be expressed and obtained in a known manner. In the case of mammalian cells, expression may be accomplished using an expression vector containing a conventionally used useful promoter, an antibody gene to be expressed, and DNA in which the poly A signal has been operably linked at 3' downstream thereof. Examples of the promoter/enhancer include human cytomegalovirus immediate early promoter/enhancer.

Additionally, as the promoter/enhancer which can be used for expression of antibody for use in the present invention, there can be used viral promoters/enhancers such as retrovirus, polyoma virus, adenovirus, and simian virus 40 (SV40), and so forth and promoters/enhancers derived from mammalian cells such as human elongation factor 1 (HEF1α) and so forth.

For example, expression may be readily accomplished by the method of Mulligan, R. C. et al. (Nature (1979) 277, 108–114) when SV40 promoter/enhancer is used, and by the method of Mizushima, S. et al. (Nucleic Acids Res. (1990) 18, 5322) when HEF1α promoter/enhancer is used.

In the case of *E. coli,* expression may be conducted by operably linking a commonly used promoter, a signal sequence for antibody secretion, and an antibody gene to be expressed. As the promoter, for example, there can be mentioned lacz promoter and araB promoter. The method of Ward, E. S. et al. (Nature (1989) 341, 544–546; FASEB J. (1992) 6, 2422–2427) may be used when lacz promoter is used, and the method of Better, M. et al. (Science (1988) 240, 1041–1043) may be used when araB promoter is used.

As a signal sequence for antibody secretion, when produced in the periplasm of *E. coli,* the pelB signal sequence (Lei, S. P. et al., J. Bacteriol. (1987) 169, 4379–4383) can be used. After separating the antibody produced in the periplasm, the structure of the antibody is appropriately refolded before use (see, for example, International Patent Application WO 96/30394).

As the origin of replication, there can be used those derived from SV40, polyoma virus, adenovirus, bovine papilloma virus (BPV), and the like. Furthermore, for amplification of the gene copy number in the host cell system, expression vectors can include as selectable markers the aminoglycoside transferase (APH) gene, the thymidine kinase (TK) gene, *E. coli* xanthine guaninephosphoribosyl transferase (Ecogpt) gene, the dihydrofolate reductase (dhfr) gene, and the like.

For the production of antibody for use in the present invention, any production system can be used, and the production system of antibody preparation comprises the in vitro or the in vivo production system.

As the in vitro production system, there can be mentioned a production system which employs eukaryotic cells and the production system which employs prokaryotic cells.

When the eukaryotic cells are used, there are the production systems which employ animal cells, plant cells, and fungal cells. Known animal cells include (1) mammalian cells such as CHO cells, COS cells, myeloma cells, baby hamster kidney (BHK) cells, HeLa cells, and Vero cells, (2) amphibian cells such as Xenopus oocytes, or (3) insect cells such as sf9, sf21, and Tn5. Known plant cells include, for example, those derived from the *Nicotiana* genus, more specifically cells derived from *Nicotiana tabacum* which is subjected to callus culture. Known fungal cells include (1) yeasts such as the *Saccharomyces* genus, more specifically *Saccharomyces cerevisiae,* or (2) filamentous fungi such as the *Aspergillus* genus, more specifically *Aspergillus niger.*

When the prokaryotic cells are used, there are the production systems which employ bacterial cells. Known bacterial cells include *Escherichia coli,* and *Bacillus subtilis.*

By introducing via transformation the gene of the desired antibody into these cells and culturing the transformed cells in vitro, the antibody can be obtained. Culturing is conducted in the known methods. For example, as the culture medium for mammalian cells, DMEM, MEM, RPMI1640, IMDM and the like can be used, and serum supplements such as fetal calf serum (FCS) may be used in combination. In addition, antibodies may be produced in vivo by implanting cells into which the antibody gene has been introduced into the abdominal cavity of an animal, and the like.

As further in vivo production systems, there can be mentioned those which employ animals and those which employ plants. When animals are used, there are the production systems which employ mammals and insects.

As mammals, goats, pigs, sheep, mice, and cattle can be used (Glaser, V., SPECTRUM Biotechnology Applications, 1993). Also as insects, silkworms can be used.

When plants are used, tobacco, for example, can be used. Antibody genes are introduced into these animals or plants, and antibodies are produced in such animals or plants, and collected. For example, antibody genes are inserted into the middle of the gene encoding protein which is inherently produced in the milk such as goat β casein to prepare fusion genes. DNA fragments containing the fusion gene into which the antibody gene has been inserted are injected to a goat embryo, and the embryo is introduced into a female goat. The desired antibody is obtained from themilk produced by the transgenic goat born to the goat who received the embryo or offsprings thereof. In order to increase the amount of milk produced containing the desired antibody produced by the transgenic goat, hormones may be given to the transgenic goat as appropriate. (Ebert, K. M. et al., Bio/Technology (1994) 12, 699–702).

When silkworms are used, baculovirus into which the desired antibody gene has been inserted is infected to the silkworm, and the desired antibody can be obtained from the body fluid of the silkworm (Maeda, S. et al., Nature (1985) 315, 592–594). Moreover, when tobacco is used, the desired antibody gene is inserted into an expression vector for plants, for example pMON 530, and then the vector is introduced into a bacterium such as *Agrobacterium tumefaciens.* The bacterium is then infected to tobacco such as *Nicotiana tabacum* to obtain the desired antibody from the leaves of the tobacco (Ma, J. K. et al., Eur. J. Immunol. (1994) 24, 131–138).

When antibody is produced in in vitro or in vivo production systems, as mentioned above, DNA encoding the H chain or L chain of antibody is separately incorporated into an expression vector and the hosts are transformed simultaneously, or DNA encoding the H chain and the L chain of antibody is integrated into a single expression vector and the host is transformed therewith (International Patent Application WO 94/11523).

8. Separation and Purification of Antibody

Antibodies expressed and produced as described above can be separated from inside or outside of the cell or from the host and then may be purified to homogeneity. Separation and purification of antibody for use in the present invention may be accomplished by affinity chromatography. As the column used for such affinity chromatography, there can be mentioned Protein A column and Protein G column. Examples of the column employing Protein A column are Hyper D, POROS, Sepharose F. F. (Pharmacia) and the like.

Alternatively, methods for separation and purification conventionally used for proteins can be used without any limitation. Separation and purification of antibody may be accomplished by combining, as appropriate, chromatography columns other than the above-mentioned affinity chromatography, filters, ultraconcentration, salting-out, dialysis and the like (Antibodies: A Laboratory Manual, Ed Harlow and David Lane, Cold Spring Harbor Laboratory, 1988). Chromatography other than affinity chromatography includes, for example, ion exchange chromatography, hydrophobic chromatography, gel-filtration and the like (Strategies for Protein Purification and Characterization: A Laboratory Course Manual, Ed Daniel R. Marshak et al., Cold Spring Harbor Laboratory Press, 1996).

9. Measurement of Antibody Concentration

The concentration of antibody obtained in the above 8 can be determined by measurement of absorbance or by the enzyme-linked immunosorbent assay (ELISA) and the like. Thus, when absorbance measurement is employed, the antibody obtained is appropriately diluted with PBS and then the absorbance is measured at 280 nm, followed by calculation using the absorption coefficient of, though different with different species and subclasses, 1.4 OD at 1 mg/ml in the case of human antibody. When the ELISA method is used, measurement is conducted as follows. Thus, 100 μl of goat anti-human IgG antibody diluted to 1 μg/ml in 0.1 M bicarbonate buffer, pH 9.6, is added to a 96-well plate (Nunc), and is incubated overnight at 4° C. to immobilize the antibody. After blocking, 100 μl each of appropriately diluted antibody of the present invention or samples containing the antibody, or 100 l of human IgG of a known concentration as the concentration standard is added, and incubated at room temperature for 1 hour. After washing, 100 μl of 5000-fold diluted alkaline phosphatase-labeled anti-human IgG antibody is added, and incubated at room temperature for 1 hour. After washing, the substrate solution is added and incubated, followed by measurement of absorbance at 405 nm using the MICROPLATE READER Model 3550 (Bio-Rad) to calculate the concentration of the desired antibody based on the absorbance of the concentration standard IgG.

10. Confirmation of Activity

Activity of an IL-8 binding-inhibition agent for use in the present invention can be confirmed by the method described below or a commonly known method.

For example, a known method can be used for the measurement of the antigen-binding activity (Antibodies: A Laboratory Manual. Ed Harlow and David Lane, Cold Spring Harbor Laboratory, 1988) and the ligand receptor binding-inhibition activity (Harada, A. et al., Int. Immunol. (1993) 5, 681–690) of anti-IL-8 antibody for use in the present invention.

As methods for determining the antigen-binding activity of anti-IL-8 antibody for use in the present invention, there can be used ELISA, EIA (enzyme immunoassay), RIA (radioimmunoassay), or the fluorescent antibody method. When ELISA is employed, for example, IL-8 is added to a 96-well plate onto which polyclonal antibody against IL-8 has been immobilized, and then samples containing the desired anti-IL-8 antibody, for example a culture supernatant of anti-IL-8 antibody-producing cells or purified antibody is added thereto. Secondary antibody that recognizes the desired anti-IL-8 antibody labeled with an enzyme such as alkaline phosphatase is added, and the plate is incubated, washed, and then the enzyme substrate such as p-nitrophenyl phosphate is added, and the absorbance is measured to evaluate the antigen-binding activity.

As methods for measuring the inhibition activity of ligand receptor binding of the anti-IL-8 antibody for use in the present invention, the conventional Cell ELISA or the ligand receptor binding assay can be used.

In the case of Cell ELISA, for example, blood cells or cancer cells expressing IL-8 receptors such as neutrophils are cultured in a 96-well plate to allow the cells to adhere there onto, which is then immobilized with paraformaldehyde etc. Alternatively, the membrane fractions of cells expressing IL-8 receptors are prepared and 96-well plates on which the fractions have been immobilized are prepared. To this are added a sample containing the desired anti-IL-8 antibody, for example a culture supernatant of anti-IL-8 antibody-producing cells or purified antibody, and IL-8 which is labeled with a radioisotope such as $^{125}$I, and then the plate is incubated, washed, and radioactivity is measured to determine the amount of IL-8 bound to the IL-8 receptor and thereby to evaluate the inhibition activity of ligand receptor binding of anti-IL-8 antibody.

In the inhibition assay of IL-8 binding to IL-8 receptors on the cells, blood cells or cancer cells expressing IL-8 receptors such as neutrophils are separated by means of centrifugation etc. to prepare a cell suspension. A solution of IL-8 labeled with a radioisotope such as $^{125}$I, or a mixture of unlabeled and labeled IL-8, and a solution comprising anti-IL-8 antibody whose concentration has been adjusted are added to the cell suspension. After incubating for a given period of time, the cells are separated, and the radioactivity of the labeled IL-8 bound onto the cell is measured.

As methods for measuring the neutrophil chemotaxis inhibiting ability of anti-IL-8 antibody for use in the present invention, a known method using chemotaxis chambers such as the one described by Grob, P. M. et al. (J. Biol. Chem. (1990) 265, 8311–8316) can be, used.

Specifically, anti-IL-8 antibody is diluted with a culture medium such as RPMI 1640, DMEM, MEM, or IMDM, and then a concentration-adjusted IL-8 is added thereto, which is dispensed into the bottom layer of the chamber partitioned up,and down by filters. Subsequently, a prepared cell suspension, for example a neutrophil suspension, is added to the upper layer of the chamber and then allowed to stand for a given period of time. Since migrating cells will adhere to the bottom surface of the filter attached to the chamber, the number of cells adhered thereto can be measured by a method using a stain or fluorescent antibody etc. Also, visual examination under the microscope or automatic measurement using a counting device can also be employed.

11. Method of Administration and Pharmaceutical Preparation

Therapeutic agents that contain as an active ingredient an IL-8 binding-inhibition agent such as anti-IL-8 antibody of the present invention may be administered, either orally or parenterally, or either systemically or locally.

For example a proteinaceous IL-8 binding-inhibition agent such as anti-IL-8 antibody of the present invention may be administered by intravenous injection such as drip infusion, intramuscular injection, intraperitoneal injection, subcutaneous injection, intraspinal injection, and the like either systemically or locally. The method of administration may be chosen, as appropriate, depending on the age and the conditions of the patient.

An IL-8 binding-inhibition agent such as anti-IL-8 antibody may be administered to a patient suffering from a disease in an amount sufficient to treat the disease and the symptoms of complications thereof or to prevent them at least partially. For example, the effective dosage is chosen from the range of 0.01 mg to 1000 mg per kg of body weight per administration. Alternatively, the dosage in the range of 5 to 2000 mg/body per patient may be chosen. However, the dosage of a preventive or therapeutic agent containing an IL-8 binding-inhibition agent such as anti-IL-8 antibody of the present invention is not limited to these dosages.

The timing of administration may be, after the onset of cerebral stroke, cerebral edema, or after reperfusion injury of cerebral ischemia. Alternatively, the timing may be at the time of reperfusion after temporal blocking of cerebral blood flow or when reperfusion is expected in a reperfusion therapy such as the thrombolytic therapy, or it may be administered when increased vascular permeability is estimated.

Preventive or therapeutic agents that contain as the active ingredient an IL-8 binding-inhibition agent such as anti-IL-8 antibody of the present invention may be formulated into a pharmaceutical preparation (Remington's Pharmaceutical Science, latest edition, Mark Publishing Company, Easton, U.S.A.), and may further contain pharmaceutically acceptable carriers or additives.

Examples of such carriers or pharmaceutical additives include water, a pharmaceutically acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, agar, polyethylene glycol, diglycerin, glycerin, prdpylene glycol, Vaseline, paraffin, stearyl alcohol, stearic acid, human serum albumin (HSA), mannitol, sorbitol, lactose, pharmaceutically acceptable surfactants and the like.

Actual additives are chosen from, but not limited to, the above or combinations thereof depending on the dosage form of a preventive or therapeutic agent of the present invention.

When anti-IL-8 antibody is used as a parenteral injection, purified anti-IL-8 antibody may be dissolved in a solvent, for example, physiological saline, a buffer, a glucose solution, etc., to which are added an anti-adsorption agent such as Tween 80, Tween 20, gelatin, human serum albumin etc. Alternatively, a lyophilized agent which is reconstituted prior to use may be used, and as an excipient for lyophilization, sugar alcohols and sugars such as mannitol, glucose etc. can be used.

12. Confirmation of preventive or therapeutic effects

For confirmation of preventive or therapeutic effects on cerebral infarction, cerebral edema, or reperfusion injury of cerebral ischemia, the focal cerebral ischemia model or the global cerebral ischemia model is used (Keiji Sano, ed., "Nosocchu Jikkenn Handbook (Handbook of Cerebral Apoplexy Experiments)," IPC, 43–51, 1990). Effects on reperfusion injury may be investigated by a transient occlusion in which blood flow is resumed after blocking cerebral blood flow for a given period of time in respective models. When no perfusion is required on the order hand, permanent occlusion is performed in which blockage of cerebral blood flow is continued.

Though animals used generally include monkeys, dogs, cats, rabbits, rats, mice, Mongolian gerbils, and the like, any species of animal can be used as long as the expression of IL-8 has been confirmed in the animal for the purpose of confirming the preventive or therapeutic effects of an IL-8 binding-inhibition agent such as anti-IL-8 antibody of the invention. In this regard, there can be mentioned rabbits, guinea pigs, pigs, dogs, sheep, monkeys, and the like.

Methods for producing focal cerebral ischemia models are broadly divided into those in which incoming cerebral vessels are compression-occluded from the outside and those in which emboli are injected. Specifically, there. can be mentioned: a method in which, for one or several strings of intracranial arteries or carotid arteries that send the blood stream to the brain such as the middle cerebral artery, the anterior cerebral artery, the posterior communicating cerebral artery, the internal carotid artery, the external carotid artery, and the tibial artery, the target artery is surgically cauterized within the framework that it does not cause global ischemia; a method in which the target artery is occluded with an artery clip; a method in which the target artery is ligated; or a method in which a photosensitive dye is intravenously given and a laser light is irradiated to the target artery to produce thrombi, and the like. Alternatively, blood coagulation factors, clots, or air is given to produce obstruction.

The method of creating the global ischemia model may comprise blocking simultaneously arteries such as the internal carotid artery, the external carotid artery, and the tibial artery at sites relatively proximal to the heart. As the method of blocking the artery, there can be mentioned a method in which the target artery is cauterized, a method in which the target artery is clipped with an artery clip, a plug method in which emboli are placed in the target artery, and the like.

In any method selected from the above, an IL-8 binding-inhibition agent such as anti-IL-8 antibody is administered at any timing such as before or immediately after ischemia, after ischemia for a given period of time, immediately before or immediately after reperfusion, or after reperfusion for a given period of time. After ischemial for a given period of time, or reperfusion for a given period of time, cerebral circulation, cerebral metabolism, and neurological functions are measured, and after the animal was sacrificed neurological pathology, infarct size, edema, increased vascular permeability and the like are evaluated.

As the method for determining cerebral circulation, there are mentioned, for example, the hydrogen clearance method, the thermocouple method, the laser Doppler method, and the like (Keiji Sano, ed., "Nosocchu Jikkenn Handbook (Handbook of Cerebral Apoplexy Experiments)," IPC, 193–240, 1990).

As the method for quantifying the infarct size, for example, the following method can be mentioned. After removing the brain, it is cut into slices with a fixed thickness. The sliced brain tissue is stained with 2,3,5-triphenyltetrazolium chloride (TTC) or the Nissl's stain to distinctively quantify the injured areas, or thin sections are prepared which are then histopathologically distinguished and quantified using the hematoxylin-eosin stain (Keiji Sano, ed., "Nosocchu Jikkenn Handbook (Handbook of Cerebral Apoplexy Experiments)," IPC, 587–623, 1990).

As the method for quantifying edema, for example, the following method can be mentioned: the method in which after the brain is removed, the specific gravity of a fixed amount of the tissue is determined using the density gradient; the method in which water content of the brain tissue is determined using the weight ratio of the wet weight and the dry weight; or the method in which it is evaluated by the nuclear magnetic resonance method (Keiji Sano, ed., "Nosocchu Jikkenn Handbook (Handbook of Cerebral Apoplexy Experiments)," IPC, 630–635, 1990).

As the method for quantifying increased vascular permeability, for example, the following method can be mentioned. Thirty minutes before sacrificing the animal used for the experiment, a given concentration of Evans blue solution is intravenously administered. After removing the brain, it is cut into slices with a fixed thickness. The area stained blue by Evans blue in the sliced brain tissue is quantified. (Keiji Sano, ed., "Nosocchu Jikkenn Handbook (Handbook of Cerebral Apoplexy Experiments)," IPC, 693–705, 1990). Additionally, it is also possible to determine cerebral edema with increased vascular permeability as an index, since increased vascular permeability also induces cerebral edema.

As the method for creating the model of subarachnoid hemorrhage, there are a method of injecting blood or a substance that is capable of inducing angiospasm into the subarachnoid cavity of an animal for which the expression of IL-8 has been confirmed or placing them after opening the head, or a method of allowing the animal to bleed by mechanically sticking a needle into or cutting cerebral vessels, etc. (Keiji Sano, ed., "Nosocchu Jikkenn Handbook (Handbook of Cerebral Apoplexy Experiments)," IPC, 124–125, 1990).

As the model of cerebral hemorrhage, there are the intracranial blood injection model, the intracranial microballoon swelling model, and the like (Keiji Sano, ed., "Nosocchu Jikkenn Handbook (Handbook of Cerebral Apoplexy Experiments)," IPC, 134–138, 1990).

EXAMPLES

The present invention will now be explained hereinbelow in more detail with reference to the following reference examples and working examples. It is to be noted that the present invention is not limited to these examples in any way.

Reference Example 1
Construction of a Hybridoma that Produces Monoclonal Antibody Against Human IL-8

Human IL-8 was given to Balb/c mice according to the conventional method, and splenocytes were collected from the mice in which immunization was established. According to the conventional method which utilizes polyethylene glycol, the splenocytes were fused with the mouse myeloma cell P3X63Ag8.653 to construct a hybridoma that produces monoclonal antibody against human IL-8. After screening using the binding activity to human IL-8 as an index, the hybridoma cell line WS-4 was obtained. Antibodies produced.by the hybridoma WS-4 had the activity of inhibiting the binding of IL-8 to neutrophils, i.e. neutralizing activity (Ko, Y. et al., J. Immunol. Methods (1992) 149, 227–235).

The isotypes of the H chain and the L chain of the antibody produced by the hybridoma WS-4 were examined using the mouse monoclonal antibody isotyping kit. The result revealed that the antibody produced by the hybridoma WS-4 has mouse κ type L chain and mouse γ1 type H chain.

The hybridoma cell line WS-4 was internationally deposited under the provisions of the Budapest Treaty on Apr. 17, 1996 with the National Institute of Bioscience and Human Technology, Agency of Industrial Science and Technology, of 1–3, Higashi 1-chome, Tsukuba-shi, Ibaraki, Japan, as FERM BP-5507.

Reference Example 2
Construction of a Humanized Antibody Against Human IL-8

The humanized WS-4 antibody was constructed as described in International Patent Application WO 96-02576.

From the hybridoma WS-4 prepared in Reference example 1, total RNA was prepared in the conventional method, and single-stranded cDNA was synthesized therefrom. By the PCR method, DNA encoding the V region of H chain and L chain of the mouse WS-4 antibody was amplified. The primers used in the PCR method are those described in Jones, S. T. and Bendig, M. M., Bio/Technology (1991) 9, 88–89. The PCR-amplified DNA fragments were purified, and the DNA fragments containing the gene encoding the L chain V region of the mouse WS-4 antibody and the DNA fragments containing the gene encoding the H chain V region of the mouse WS-4 antibody were isolated. These DNA fragments were ligated to respective plasmid pUC cloning vector, which was then introduced into competent E. coli cells to obtain E. coli transformant.

The transformant was cultured in the conventional method, and from the cells thus obtained a plasmid containing the above DNA fragments was purified. The base sequence of DNA encoding the V region in the plasmid was determined in the conventional method, and the CDR of each v region was identified from the amino acid sequence.

In order to construct vectors that express chimera WS-4 antibody, cDNA's encoding the V region of L chain and H chain of mouse WS-4 antibody were separately inserted into respective HEF vectors that were previously ligated to DNA encoding human C region.

In order to construct humanized WS-4 antibody, genetic engineering technique based on the CDR grafting method was used to implant the CDR of V region of mouse WS-4 antibody to human antibody. In order to form appropriate antigen-binding sites, substitution of DNA sequences for partial substitution of amino acids of the FR of V region of CDR-implanted antibody was conducted.

In order to express the V regions of L chain and H chain of humanized WS-4 antibody thus constructed as antibody in a mammalian cell, DNA encoding each was separately inserted into HEF vector, and a vector expressing the L chain or the H chain of humanized WS-4 antibody was constructed.

By simultaneously transfecting these two expression vectors into COS cells, a cell line that produces humanized WS-4 antibody was established. The ability to bind to and neutralizing IL-8 of the humanized WS-4 antibody obtained by culturing the thus obtained cell line was evaluated by ELISA and the inhibition test of IL-8/neutrophil binding, respectively. The results revealed that the humanized WS-4 antibody inhibits the binding of IL-8 to neutrophil by binding to human IL-8 in an extent similar to that of mouse WS-4 antibody.

E. coli having the plasmid containing the L chain or the H chain of humanized WS-4 antibody was internationally deposited under the provisions of the Budapest Treaty as Escherichia coli DH5α (HEF-RVLa-gκ) and Escherichia coli JM109 (HEF-RVHg-gγ1) on Jul. 12, 1994 with the National Institute of Bioscience and Human Technology, Agency of Industrial Science and Technology, of 1–3, Higashi 1-chome, Tsukuba city, Ibaraki pref., Japan, as FERM BP-4738 and FERM BP-4741, respectively.

Example 1

To female New Zealand white rabbits weighing 2.7 to 3.0 kg (Sankyo Lab Service) was given 0.5 mg of atropine sulfate (Tanabe Pharmaceutical) intramuscularly and then the animals were mask-anethsetized with a 3% isoflurane (Abbott)-mixed air. The dripping path was secured by fixing SURFLO indwelling needle 24G (Terumo) to the auricular vein and running an appropriate amount of the lactate Ringer solution(Ohtsuka Pharmaceutical) thereinto. After fixing the animals in the supine position on the operating table, and shaving the anterior region of the neck and the right femoral region, the trachea was exposed by dissecting the anterior region of the neck, and a tube was inserted in place by bronchial intubation after tracheostomy, and was connected to the artificial respirator (Shinano).

Simultaneously with the connection to the artificial respirator, 2 mg of pancuronium bromide (Organon Teknica) was intravenously given, and the partial pressure of carbon dioxide in the artery was adjusted to be 32 to 40 mmHg under the condition of 1.5% isoflurane, 30% oxygen, the tidal air volume 15 to 20 ml/kg, and the ventilation frequency 20 to 25 per minute. After dissecting the femur, the femoral artery was ablated, and Surflow indwelling needle 24G (Terumo) was placed therein and connected to the blood pressure monitor (Nippon Koden) to measure blood pressure continuously till the end of the experiment. Subsequently, the rabbits were placed at the prone position and the head was fixed to the localization frame. The supplement lactate Ringer solution (Ohtsuka Pharmaceutical) supplemented with 0.16 mg/ml pancuronium bromide was intravenously given via the auricular vein at 5 ml/kg/hr with a syringe pump on a continuous basis.

The scalp at the fronto occipital circumference of the right eyeball of the rabbit under anesthesia was dissected and ablated, and the eyeball and the contents in the orbital were extirpated under hemostasis. The optic canal was expanded using a drill to open the dura, before the internal carotid artery, the middle cerebral artery (MCA), and the anterior cerebral artery were exposed and ablated.

Under the operating microscope, the internal carotid artery, the origin of the middle cerebral artery, and the origin of the anterior cerebral artery were obstructed with the ZEN clip to create the middle cerebral artery occlusion model. In order to prevent influx from the collateral circulation, the concentration of isoflurane was adjusted to be about 3% and the average blood pressure was maintained at 50 to 60 mmHg during ischemia. Focal ischemia of the right brain for 2.5 hours at ordinary temperature was initiated by obstruction with the clip. After 2.5 hours of ischemia, the concentration of isoflurane was returned to about 1% and the normal blood pressure was regained, before the clip was released to start reperfusion.

As the control, the permanent occlusion group was prepared in which cerebral ischemia with the clip but without reperfusion was performed. At the completion of each experiment, 2 ml of 2M potassium chloride was. rapidly given intravenously to sacrifice the animals and then the animals were evaluated for the following points.

1) IL-8 Concentration in the Brain Tissue

The brain was excised and 150 mg of the brain tissue in the territory of the right middle cerebral artery was collected, which was fully homogenized in 300 µl of PBS. Subsequently, it was centrifuged at 10,000 rpm for 5 minutes in the microcentrifuge, and the supernatant was recovered and stored at −80° C. until the measurement of IL-8 concentration. IL-8 concentration was measured in the following method based on ELISA. First, mouse IL-8 antibody WS-4 was diluted to 0.5 µg/ml in 50 mM sodium bicarbonate buffer, pH 9.6, and a 100 µl aliquot was dispensed to each well of a 96-well microtiter plate (Nunc) and then was immobilized by incubating overnight at 4° C.

After washing three times with 0.05% Tween 20-added PBS (Tween-PBS), 150 µl of a 1% bovine serum albumin (BSA)-added PBS was dispensed to each well, followed by incubation at 37° C. for one hour. After washing three times with Tween-PBS, 100 µl of a sample diluted with 0.5% BSA-added Tween-PBS was added. In order to prepare the standard curve for IL-8 concentration, recombinant rabbit IL-8 was diluted to a concentration of 13.7 to 10,000 pg/ml with 0.5% BSA-added Tween-PBS, and 100 µl aliquots thereof were plated to separate wells. Subsequently, the plate was incubated overnight at 4° C. After washing the plate with Tween-PBS for five times, guinea pig anti-rabbit IL-8 antibody as the primary antibody was diluted to 1 µg/ml with 3% PEG 6000-added Tween-PBS, and a 100 µl aliquot was added to each well, which was incubated at 37° C. for 2 hours.

After washing five times with Tween-PBS, alkaline phosphatase-labeled anti-guinea pig IgG antibody (BioMakor) as the secondary antibody was diluted 5000-fold with 0.5% BSA-added Tween-PBS, and a 100 µl aliquot was added to each well, which was incubated at 37° C. for 2 hours. After washing five times with Tween-PBS, disodium p-nitro phenyl phosphate was dissolved in 1 µg/ml with 1 M diethanolamine, pH 9.8, and a 100 µl aliquot was added to each well, which was incubated at room temperature for 30 minutes. In order to stop the reaction a 100 µl aliquot of 1 N sodium hydroxide was added to each well, absorbance of which was measured at 405 nm using the microplate. reader (Toso), and IL-8 concentration in the sample was calculated based on the standard curve. Concentration was expressed in terms of 100 mg tissue/100 µl PBS (FIG. 1).

IL-8 concentration of each of the 2.5 hour ischemia group, the 2.5 hour ischemia and 3 hour reperfusion group, and the 2.5 hour ischemia and 6 hour reperfusion group was 75.0±41.4 pg/ml, 69.2±41.0 pg/ml, and 461.5±77.1 pg/ml, respectively. In each of the 5.5 hour ischemia group and the 8.5 hour ischemia group, it was 103.5±44.4 pg/ml and 143.8±20.0 pg/ml, respectively (the values represent mean± standard error). In the 2.5 hour ischemia and 6 hour reperfusion group, a significantly high concentration of IL-8 was detected as compared to the 2.5 hour ischemia and 3 hour reperfusion group, and the 8.5 hour ischemia group (p<0.05). This revealed that IL-8 was produced in the ischemic brain and it becomes remarkably elevated after 3 hours reperfusion.

2) The Effects of WS-4 Antibody on the Disruption of the Blood Brain Barrier During Cerebral Infarction In order to investigate the effects of WS-4 antibody on the disruption of the blood brain barrier during cerebral infarction, a group was prepared in which WS-4 antibody was administered immediately after the start of reperfusion by releasing the clip in the 2.5-hour ischemia and 6 hour reperfusion experiment. Ten milligrams of WS-4 antibody was diluted with 3 ml of physiological saline, which was injected via the auricular vein before 6 hours of reperfusion was performed. As the negative control, 10 mg of mouse antibody (P3.6.2.8.1) was similarly injected intravenously. Evans blue (Nakalai Tesque) was dissolved to 3% in the lactate Ringer solution. After 6 hours of reperfusion, 5 ml of the solution was injected via the auricular vein, and 30 minutes later the brain was excised. The brain was cut into 2 mm slices using the rabbit brain slicer (ASI), and photographs were taken of the 6 slices containing the area 5 mm anterior to and 5 mm posterior to the chlasma opticum. The area of the right brain and the area of the region stained with Evans blue were measured, and the ratio of volume of the 6 slices in the right brain was calculated (FIG. 2).

In the normal brain, Evans blue cannot permeate through the blood vessel due to the function of the blood brain barrier, and therefore Evans blue cannot stain the parenchyma of the brain. However, in the 2.5-hour ischemia and 6-hour reperfusion experiment, the percentage of the Evans blue-stained volume to that of the area 5 mm anterior to and 5 mm posterior to the chiasma opticum was 17.6±3.2% in the group (N=9) in which the control antibody (P3.6.2.8.1) was intravenously injected immediately after the start of reperfusion, indicating that the blood brain barrier has been disrupted and vascular permeability is enhanced. On the other hand, the percentage of the Evans blue-stained volume in the WS-4 antibody administration group (N=9) was a remarkably low 7.8±1.2%. The Mann Whitney U-test of the result revealed a statistically significant difference (p<0.05).

Accordingly, the disruption of the blood brain barrier and increased vascular permeability in the ischemia reperfusion were inhibited by the intravenous administration of WS-4 antibody. The fact can be interpreted as showing that the intravenous administration of WS-4 antibody inhibited cerebral edema.

3) The Effects of WS-4 Antibody on the Formation of the Cerebral Infarct

In order to investigate the effects of WS-4 antibody on the formation of the cerebral infarct, a 2.5-hour ischemia and 12-hour reperfusion experiment was performed. For the purpose of elucidating the effects on the infarct, the reperfusion time was extended from the above 6 hours to 12 hours in expectation of enhanced formation of the infarct.

In order to measure blood flow in the territory of middle cerebral artery at the surface of the brain, a circular window of 7 mm in diameter was opened using a drill at a position 1 cm right to the fontanel point to expose the dura. A probe (ST-N, Omega Flow) of the non-contact type laser Doppler blood flowmeter (FLO-N1, Omega Flow) was fixed to the localization frame, and by irradiating the window the cerebral blood flow was measured till the end of the experiment. When, compared to the blood flow of the normal brain, an individual has shown a decrease to 70% or lower in the flow after occlusion with the clip, and a restoration of 30% or greater in the blood flow after releasing the clip, the individual was adopted into the ischemia reperfusion group. The number eventually adopted was N=7 in the both of the WS-4 antibody administration group and the control antibody administration group.

Immediately after starting reperfusion by releasing the clip, 10 mg of WS-4 antibody was given via the auricular vein, and 12-hour reperfusion was performed. As the negative control group, 10 mg of mouse antibody (P3.6.2.8.1) was similarly given intravenously. After 12-hour reperfusion, the brain was excised, and made into slices of 2 mm in thickness and the 6 slices containing the area 5 mm anterior to and 5 mm posterior to the chiasma opticum were immersed in a physiological saline (Ohtsuka Pharmaceutical) containing 2% TTC (Wako Pure Chemical Industries), and incubated at 37° C. for 30 minutes.

This method stains the normal tissue red but not the infarct thereby enabling the quantification of the infarct. Each slice was photographed and then the area of the right brain and that of the region which was not stained with TTC were measured to calculate the percentage of the volume the infarct occupied by the slices containing the area 5 mm anterior to and 5 mm posterior to the chiasma opticum in the right brain (FIG. 3).

As a result, the volume of the infarct in the area 5 mm anterior to and 5 mm posterior to the chiasma opticum in the control antibody (P3.6.2.8.1) administration group was $40.1 \pm 10.7\%$. On the other hand, the volume of the infarct in the WS-4 antibody administration group remarkably decreased to $14.9 \pm 7.5\%$. Statistical analysis by the Mann Whitney U-test of the result revealed a statistically significant difference ($p<0.05$). Accordingly, the formation and development of the infarct during reperfusion of cerebral ischemia was inhibited by the intravenous administration of WS-4 antibody.

These results revealed that anti-IL-8 antibody has the effect of inhibiting the disruption of the blood brain barrier and the formation and development of the cerebral infarct during cerebral infarction. It is also expected that anti-IL-8 antibody will be a preventive or therapeutic agent for cerebral infarction for which the effective dose time span is longer than the conventional drugs since IL-8 production increased with time in the permanent occlusion group and the reperfusion group,.

Industrial Applicability

Administration of an IL-8 binding-inhibition agent such as anti-IL-8 antibody inhibited the disruption of the blood brain barrier due to increased vascular permeability and the formation of an infarct during cerebral ischemia. This fact indicates that an IL-8 binding-inhibition agent such as anti-IL-8 antibody is useful as a preventive or therapeutic agent for cerebral stroke, cerebral edema or reperfusion injury of cerebral ischemia, and increased cerebral vascular permeability.

What is claimed is:

1. A method to treat cerebral infarction, which method comprises systemically administering to a subject in need of such treatment an amount of an anti-IL-8 antibody effective to treat the cerebral infarction.

2. The method of claim 1 wherein the anti-IL-8 antibody is a monoclonal antibody.

3. The method of claim 1 wherein the anti-IL-8 antibody is prepared by immunizing an animal with mammalian IL-8.

4. The method of claim 3 wherein the anti-IL-8 antibody is prepared by immunizing an animal with human IL-8.

5. The method of claim 1 wherein the anti-IL-8 antibody is WS-4 secreted by the hybridoma deposited as accession number FERM BP-5507.

6. The method of claim 1 wherein the anti-IL-8 antibody is a humanized or chimeric antibody.

7. The method of claim 6 wherein the anti-IL-8 antibody is humanized WS-4, wherein the light chain of the antibody is encoded by the plasmid in *E. coli* DH5 deposited as accession number FERM BP-4738 and wherein the heavy chain of the antibody is encoded by the plasmid in *E. coli* JM109 deposited as FERM BP-4741.

8. The method of claim 1 wherein the cerebral infarction is hemodynamic infarction.

* * * * *